(12) United States Patent
Deininger et al.

(10) Patent No.: US 7,860,568 B2
(45) Date of Patent: Dec. 28, 2010

(54) LEAD RETENTION ASSEMBLY FOR IMPLANTABLE MEDICAL DEVICE

(75) Inventors: Steve T. Deininger, Blaine, MN (US); Jeffrey J. Clayton, Ramsey, MN (US); Charles Edward Peters, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 371 days.

(21) Appl. No.: 12/107,828

(22) Filed: Apr. 23, 2008

(65) Prior Publication Data
US 2009/0270940 A1    Oct. 29, 2009

(51) Int. Cl.
*A61N 1/375* (2006.01)
(52) U.S. Cl. ........................................ 607/37
(58) Field of Classification Search .................. 607/36, 607/37; 439/190, 288, 309
See application file for complete search history.

(56) References Cited

U.S. PATENT DOCUMENTS

| | | | |
|---|---|---|---|
| 3,760,332 A | 9/1973 | Berkovits |
| 4,072,154 A | 2/1978 | Anderson |
| 4,141,752 A | 2/1979 | Shipko |
| 4,262,673 A | 4/1981 | Kinney |
| 4,461,194 A | 7/1984 | Moore |
| 4,934,366 A | 6/1990 | Truex |
| 5,906,634 A | 5/1999 | Flynn |
| 6,029,089 A | 2/2000 | Hawkins |
| 6,505,073 B2 | 1/2003 | Gramse |
| 7,110,819 B1 | 9/2006 | O'Hara |
| 7,174,211 B2 | 2/2007 | Spadgenske |
| 2006/0247716 A1 | 11/2006 | Fruland |
| 2007/0100386 A1 | 5/2007 | Tronnes |
| 2007/0265674 A1 | 11/2007 | Olson |

FOREIGN PATENT DOCUMENTS

EP    0 006 281    1/1980

OTHER PUBLICATIONS

Tyers, G.F. et al., Analysis of set screw and side-lock connector reliability, Pacing and Clinical Electrophysiology: Pce Nov. 1992, vol. 15, No. 11.
PCT International Search Report and Written Opinion dated May 27, 2009.

*Primary Examiner*—Carl H Layno
*Assistant Examiner*—Brian T Gedeon
(74) *Attorney, Agent, or Firm*—John W. Albrecht; Campbell Nelson Whipps LLC

(57) ABSTRACT

A lead retention assembly for an implantable medical device includes (i) a conductive set screw and (ii) a housing defining an opening for receiving at least a portion of the set screw. The assembly further includes a block disposed within the housing. The block defines a lead receiving bore and a second bore extending generally perpendicular to and intersecting with the lead receiving bore. The assembly further includes a conductive lead engagement member having a lead engagement feature. The lead engagement feature is disposed within and movable within the second bore such that advancement of the set screw causes the lead engagement feature to move within the second bore towards the lead receiving bore. The set screw is electrically isolated from the conductive lead engagement member.

20 Claims, 13 Drawing Sheets

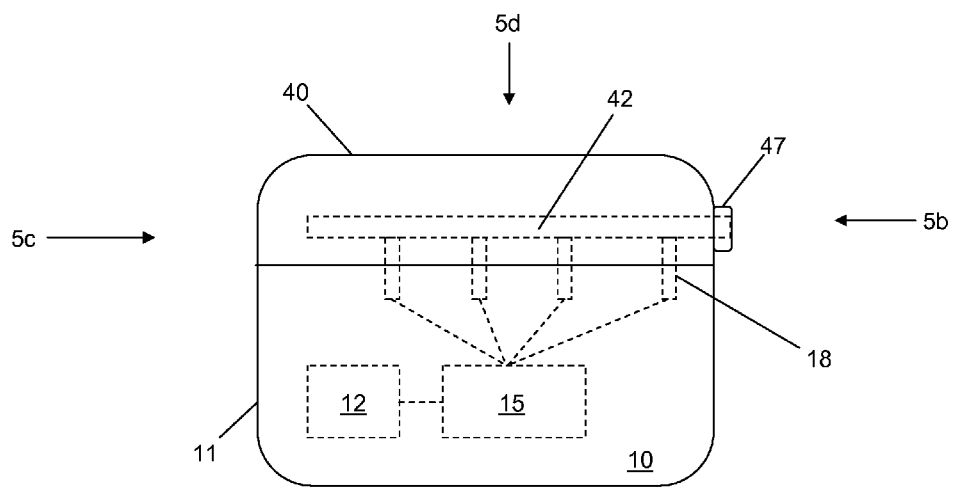
FIG. 5A
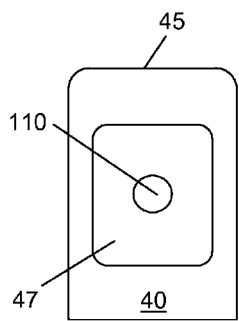 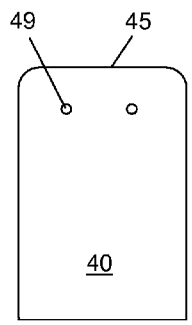 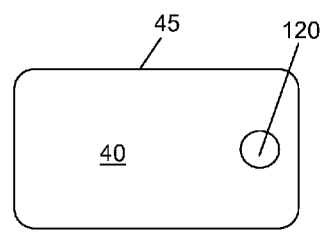
FIG. 5B    FIG. 5C    FIG. 5D

LEAD RETENTION ASSEMBLY FOR IMPLANTABLE MEDICAL DEVICE

FIELD

This application relates to medical devices, more particularly to implantable medical devices operably couplable to leads or lead extensions and to lead retention assemblies for operably coupling the leads to the devices.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes disposed on a distal end portion of a lead. The proximal end portion of a lead typically contains a number of connector rings corresponding to the number of electrodes. Conductors run within and along the lead body and electrically couple the connectors to the electrodes. The proximal end portion of the lead is inserted into lead receptacle of a signal generator such that electrical contact is made between discrete contacts in the connector portion and the connector rings of the lead. The lead is then typically secured within the lead receptacle of the signal generator via a set screw, which provides a compressive force on the lead, typically at one of the connector rings. In such cases, the set screw and associated lead retention assembly serve to not only retain the lead within the receptacle but also provide an electrical connection with the signal generating electronics of the device.

When the set screw and associated lead retention assembly are used for purposes of electrical coupling of a lead to signal generating electronics of the device, care is taken to prevent inadvertent stimulation of tissue in the vicinity of the set screw. Such "pocket stimulation" is typically prevented by electrically isolating the set screw from tissue of the patient in which the device is implanted. Electrical isolation is often achieved by placing a silicone grommet between the set screw and the outer surface of the device. The grommet includes a slit to allow a screw driver access to the set screw. However, if the grommet tears or rips during the process of tightening the screw, the electrical insulating properties of the grommet are compromised.

Others have proposed using a plastic set screw or a composite set screw with a plastic head to prevent pocket stimulation, where the nonconductive plastic portion of the set screw serves to electrically insulate the conductive portions of the set screw or conductive portions of the lead retention assembly from tissue of the patient. However, plastic set screws or set screws having plastic heads may strip more easily than their metallic counterparts. If the set screw strips, it may not be adequately tightened to retain the lead or may not be able to be removed should a lead replacement be desired.

BRIEF SUMMARY

Lead retention assemblies having conductive set screws, such as metallic set screws, that are electrically isolated or insulated from electronics of an active implantable medical device are described herein.

For example, a lead retention assembly for an implantable medical device may include (i) a conductive set screw and (ii) a housing defining an opening for receiving at least a portion of the set screw. In various embodiments, the opening of the housing is internally threaded and configured to threadingly engage an externally threaded portion of the set screw. The assembly further includes a conductive block disposed within the housing. The conductive block defines a lead receiving bore and a second bore extending generally perpendicular to and intersecting with the lead receiving bore. The assembly further includes a lead engagement member having a lead engagement feature. The lead engagement feature is disposed within and movable within the second bore such that advancement of the set screw causes the lead engagement feature to move within the second bore towards the lead receiving bore. The set screw is electrically isolated from the conductive block. For example, the lead engagement member may be formed of nonconductive material and may, at least in part, electrically isolate the set screw from the conductive block. By way of further example, the assembly may further include a nonconductive member configured to at least in part electrically isolate the set screw from the conductive block. The nonconductive member is disposed within the housing such that advancement of the set screw causes the nonconductive member to cause the lead engagement feature to move within the second bore towards the lead receiving bore. In various embodiments, the opening of the housing, the set screw, the nonconductive member, and the lead engagement member are axially aligned.

By way of further example, a lead retention assembly for an implantable medical device may include (i) a conductive set screw and (ii) a housing defining an opening for receiving at least a portion of the set screw. The opening of the housing may be internally threaded and configured to threadingly engage an externally threaded portion of the set screw. The assembly further includes a block disposed within the housing. The block defines a lead receiving bore and a second bore extending generally perpendicular to and intersecting with the lead receiving bore. The assembly further includes a conductive lead engagement member having a lead engagement feature. The lead engagement feature is disposed within and movable within the second bore such that advancement of the set screw causes the lead engagement feature to move within the second bore towards the lead receiving bore. The set screw is electrically isolated from the lead engagement member. For example, the assembly may further include a nonconductive member configured to at least in part electrically isolate the set screw from the conductive block. The nonconductive member is disposed within the housing such that advancement of the set screw causes the nonconductive member to cause the lead engagement feature to move within the second bore towards the lead receiving bore. In various embodiments, the opening of the housing, the set screw, the nonconductive member, and the lead engagement member are axially aligned.

Methods for manufacturing a lead retention assembly for an implantable medical device are also described herein. In various embodiments, the methods include axially aligning a second bore of a conductive block with an opening in a housing of the assembly. The conductive block defines the second bore and a lead receiving first bore extending generally perpendicular to and intersecting with the lead receiving bore. The opening of the housing is configured to threadingly engage a set screw. The method further includes (i) placing a lead engagement feature of a lead engagement member within the second bore of the conductive block, (ii) inserting a molding pin through the opening pin and pressing the engagement feature towards the conductive block, (iii) flowing a sealing material into the housing and around the molding pin, and (iv) removing the molding pin to create a cavity formed by the sealing material such that the cavity is in communication with the opening and is axially aligned with the opening and the lead engagement member. The method further includes placing a nonconductive member in the cavity between the opening of the housing and the lead engagement member. The nonconductive member includes an exterior surface and interior surface defining a set screw receiving cavity. The nonconductive member is placed in the cavity formed by the sealing material such that exterior surface of the nonconductive member sealingly engages the sealing material.

In some embodiments, the methods include axially aligning a second bore of a block with an opening in a housing of the assembly. The block defines the second bore and a lead receiving first bore extending generally perpendicular to and intersecting with the lead receiving bore. The opening of the housing is configured to threadingly engage a set screw. The method further includes (i) placing a conductive lead engagement feature of a conductive lead engagement member within the second bore of the block, (ii) inserting a molding pin through the opening pin and pressing the engagement feature towards the block, (iii) flowing a sealing material into the housing and around the molding pin, and (iv) removing the molding pin to create a cavity formed by the sealing material such that the cavity is in communication with the opening and is axially aligned with the opening and the lead engagement member. The method further includes placing a nonconductive member in the cavity between the opening of the housing and the lead engagement member. The nonconductive member includes an exterior surface and interior surface defining a set screw receiving cavity. The nonconductive member is placed in the cavity formed by the sealing material such that exterior surface of the nonconductive member sealingly engages the sealing material.

By employing a conductive set screw the likelihood of stripping associated with nonconductive plastic set screws or screw heads is reduced. Further, by electrically isolating the set screw from electronics of an active implantable medical device, the use of grommets or other seals that tend to be subject to ripping or tearing can be avoided. These and other advantages will be readily understood from the following detailed descriptions when read in conjunction with the accompanying drawings.

BRIEF DESCRIPTION OF THE DRAWINGS

FIG. 5A is a schematic diagram of a side view of an active implantable medical device with representative internal components shown in dashed lines.

FIG. 5B is a schematic diagram of a front view of the device depicted in FIG. 5A viewed along line 5b of FIG. 5A.

FIG. 5C is a schematic diagram of a back view of the device depicted in FIG. 5A viewed along line 5c of FIG. 5A.

FIG. 5D is a schematic diagram of a top view of the device depicted in FIG. 5A viewed along line 5d of FIG. 5A.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable electrical device" or the like refers to a device that is capable of generating, sending or receiving an electrical signal via a medical lead.

The present disclosure relates to implantable medical devices, such as active electrical implantable medical devices that include a lead retention assembly for securing a lead or lead extension or other adaptor relative to the device. In various embodiments described herein, the lead retention assembly also serves to electrically couple a lead to electronics of the device. A conductive set screw, such as a metallic set screw, is employed and may be in fluid communication with tissue of a patient when the device is implanted. To avoid pocket stimulation, the set screw can be electrically isolated from the electronics the device as described herein.

Figure 1:
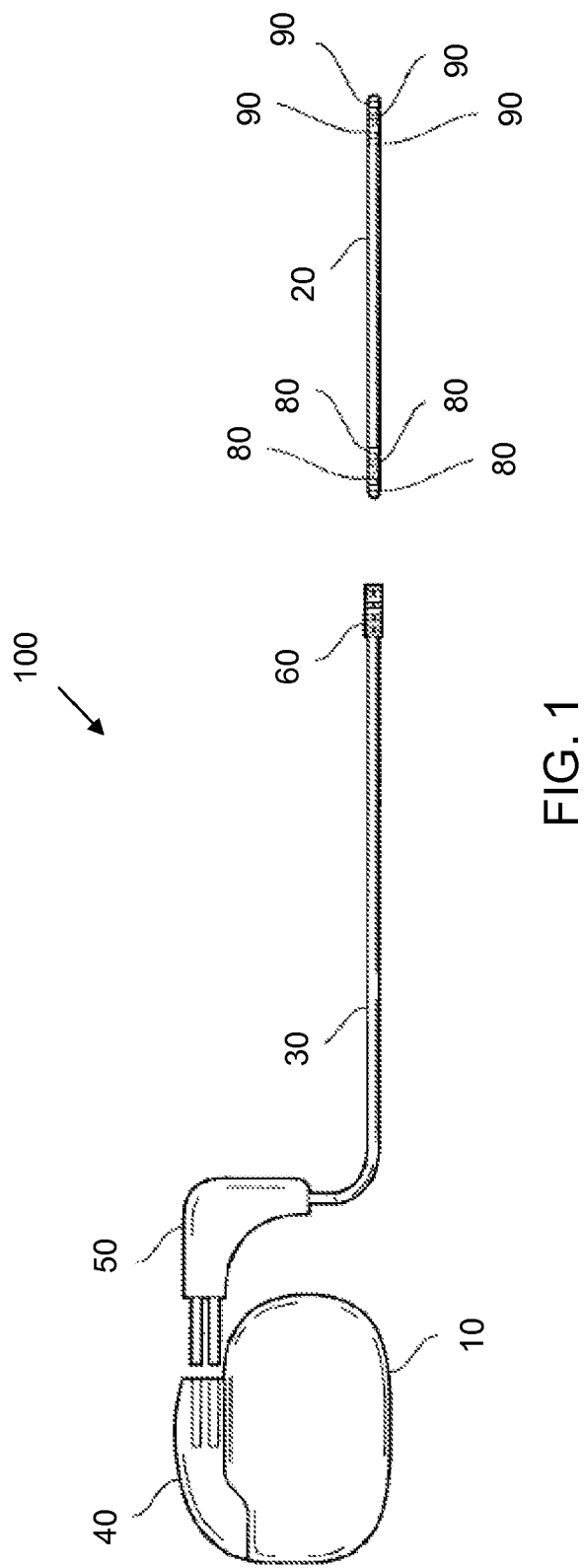
FIG. 1 is a schematic diagram of an exploded view of a representative implantable active electrical device and associated lead and extension.

Referring to FIG. 1, a schematic of an exploded view of a representative implantable medical device system 100 is shown. The system 100 includes an implantable active electrical device 10, and a lead 20 operably couplable to active electrical device 10. Active electrical device 10 may be any electrical signal generator or receiver useful for delivering therapy to a patient or for patient diagnostics. For example, active electrical device 10 may be a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. As shown in FIG. 1, the system 100 may include a lead extension 30 or other adaptor to couple lead 20 to active electrical device 10. While not shown, it will be understood that more than one lead 20 may be operably coupled to one active electrical device 10 or one extension 30 or that more than one extension 30 may be operably coupled to one active electrical device 10. It will also be understood that lead 20 may be coupled to active electrical device 10 without extension 30 or adaptor.

Active electrical device 10 may include a connector header 40 for connecting to lead 20 or extension 30 or other adaptor to couple lead 20 to active electrical device 10. In the embodiment depicted in FIG. 1, the connector header 40 is configured to receive a proximal connector portion 50 of a lead extension 30. The extension 30 includes a distal connector 60 configured to receive proximal end of lead 20. Distal connector 60 has internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown) within the body of the lead 20. Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

Figure 2:
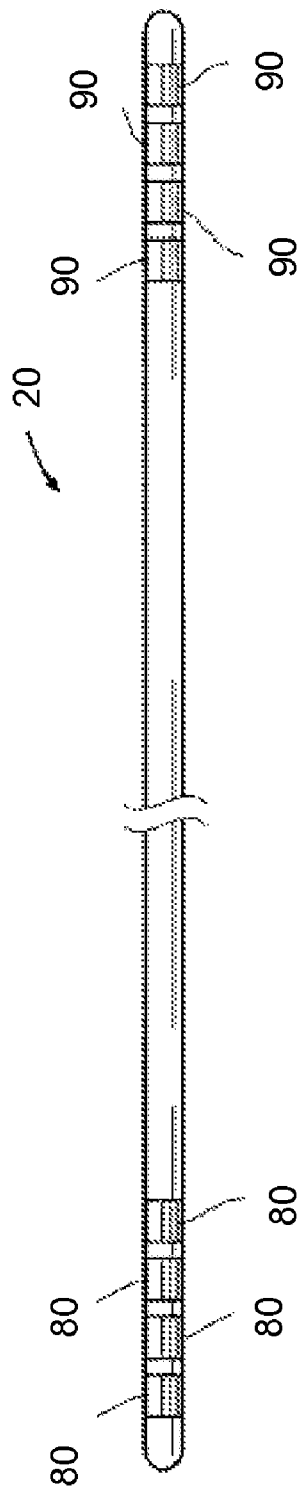
FIG. 2 is a schematic diagram of a perspective view of a representative lead.
Figure 3:
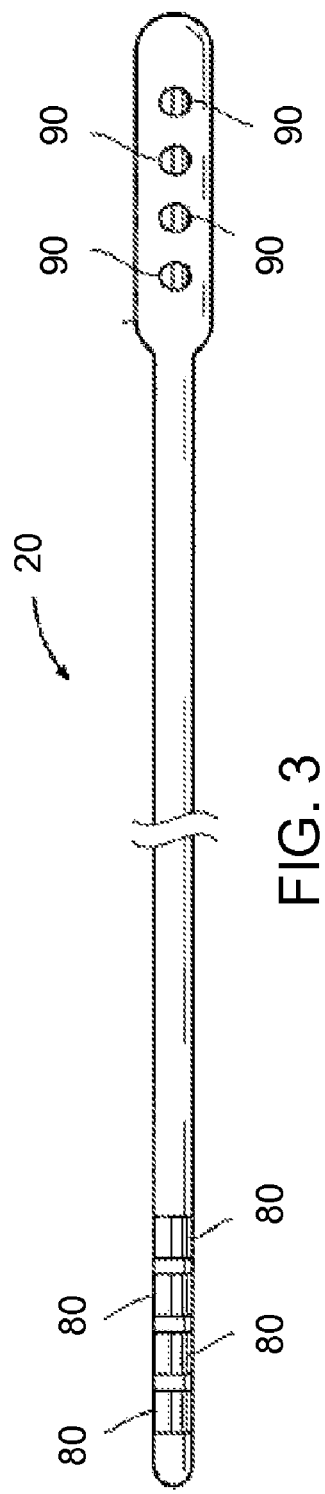
FIG. 3 is a schematic diagram of a perspective view of a representative lead.

FIGS. 2 and 3 are schematic perspective views of representative leads 20. Leads 20, as shown in FIGS. 2 and 3, contain four exposed electrical contacts 80 and four electrodes 90. However, it will be understood that a lead 20 may include any number of contacts 80 or electrodes 90, such as 1, 2, 3, 4, 8, 16, 32, or 64. The contacts 80 are typically electrically coupled to the electrode 90 via conductors (not shown) running within the lead body. Typically each contact 80 is operably coupled to a discrete contact in an active electrical medical device such that a discrete electrical signal may be applied to each electrode 90 or electrode pair. The lead contacts 80 may be electrically coupled to the device via direct insertion into a receptacle of the device or via an extension or adaptor (see, e.g., FIG. 1). The lead 20 shown in FIG. 3 is a paddle-type lead. However, it will be understood that any lead configuration may be employed in accordance with the teachings provided herein.

Figure 4:
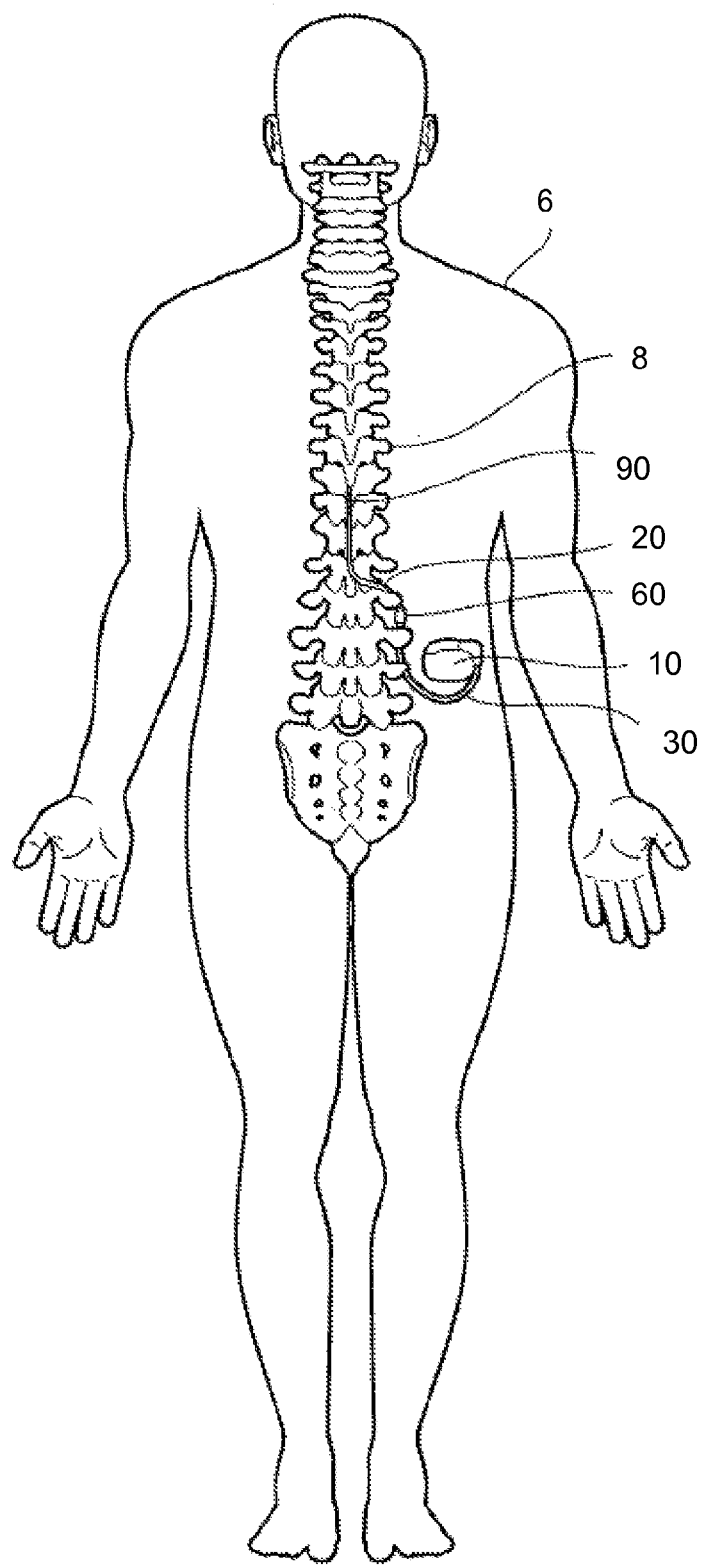
FIG. 4 is a schematic diagram of a representative spinal cord stimulation (SCS) system implanted in a patient.

By way of example and referring to FIG. 4, a spinal cord stimulation (SCS) system, is shown implanted in a patient 6. For SCS, an electrical signal generator 10 is typically placed in a medically appropriate location of the patient 6, such as in the abdominal or pectoral region, and distal portion of lead 20 containing electrodes 90 is placed at a desired location along spinal cord 8. The proximal portion of lead 20 is connected to distal connector 60 of lead extension 30, which is connected to device 10. Such a system, or any system including an electrical signal generator 10 as described herein, may also include an external programmer (not shown), such as a physician programmer or a patient programmer, for telemetric communication with the electrical signal generator 10. Electrical signal generator 10 is capable of generating electrical signals that may be applied to tissue of patient 6 via electrodes 90 for therapeutic or diagnostic purposes. Electrical signal generator 10 contains a power source and electronics for sending electrical signals to the spinal cord 8 via electrodes 90 to provide a desired therapeutic effect. It will be appreciated that other systems employing active electrical devices and therapeutic uses thereof are contemplated.

Referring now to FIG. 5A, a schematic side view of a representative active implantable electrical device 10 is shown, with selected internal components shown in dashed lines. The device 10 includes a header 40 having a lead receptacle 42 extending therein. The lead receptacle 42 is configured to receive a proximal portion of a lead, extension or adaptor. A block or block housing 47 of the lead receptacle may extend beyond the housing of the header 40. The receptacle 42 includes one or more electrically conductive portions (not shown) configured to electrically couple with proximal contacts 80 of a lead 20 (see, e.g., FIGS. 2-3) or lead extension. The conductive portions are electrically coupled to electronics 15 disposed within device housing 11. Hermetically sealed electrical feedthroughs 18 may be used to couple conductive portions of the receptacle 42 to the electronics 15. In the depicted embodiment, the electronics 15 are operably coupled to a power source 12, such as a battery, capacitor, or the like. The header 40 may be attached to hermetically sealed housing 11 of device 10 by, for example, fasteners, adhesives, welds, or the like.

In some embodiments (not shown), the lead receptacle 42 extends within hermetically sealed housing 11. In such embodiments, device 10 may not include a header 40 and feedthroughs 18. Any suitable hermetically sealed receptacle may be employed in such embodiments, such as those described in U.S. patent application Ser. No. 11/733,247, filed on Apr. 10, 2007, entitled "Hermetic Lead Connector Assembly", which application is hereby incorporated herein by reference in its entirety to the extent that it does not conflict with the disclosure presented herein.

Referring now to FIG. 5B, a schematic front view of the header 40 along line 5*b* in FIG. 5A is shown. A block or block housing 47 of the lead receptacle extends beyond the front face of the header 40 and defines a bore 110 configured to receive a proximal end of a lead. Bore 110 extends through an opening (not shown) in housing 45 of header 40. Lead receptacle, in some embodiments, does not include a block or block housing 47 that extends beyond the header housing 45.

Referring now to FIG. 5C, a schematic back view of the header 40 along line 5*c* in FIG. 5A is shown. One or more holes 49 are defined by housing 45 of header 40. The openings 49 provide fluid communication between outside and inside the housing 45.

In FIG. 5D, a top view of the header 40 along line 5*d* in FIG. 5A is shown. The housing 45 of header 40 defines an opening 120 for receiving a set screw for assisting in retaining a lead in the receptacle.

Figure 5E:
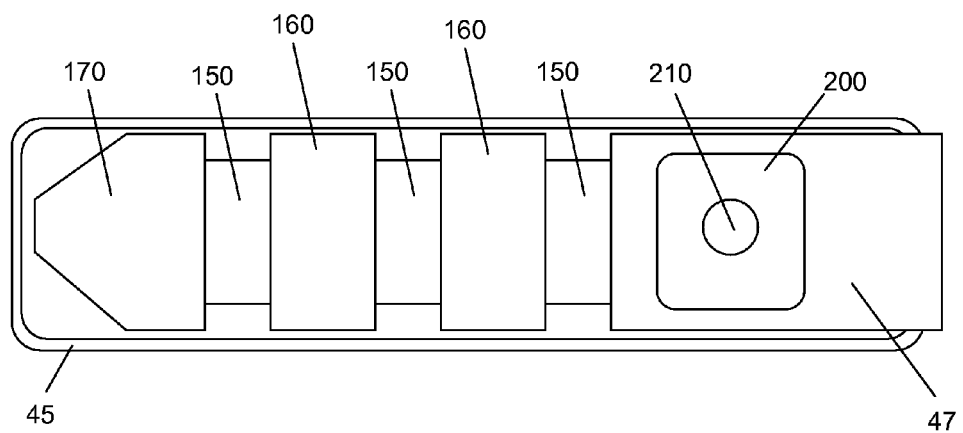
FIGS. 5E and 5G are schematic diagrams of a cut away top views of alternative embodiments of the device depicted in FIG. 5A.
Figure 5F:
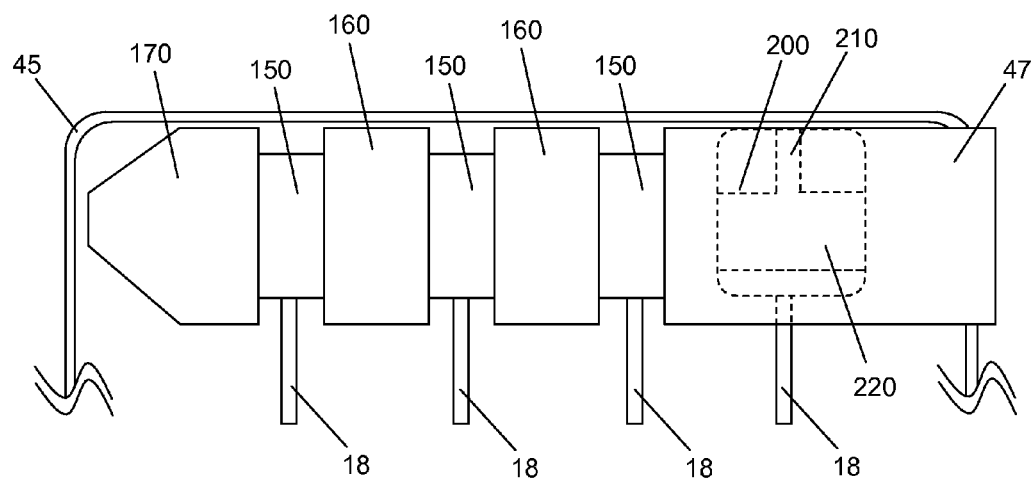
FIGS. 5F and 5H are schematic diagrams of a cut away side views of alternative embodiments of the device depicted in FIG. 5A with representative internal components shown in dashed lines.

In FIGS. 5E-F, schematics of a cut away top view (5E) and a cut away side view (5F) of the header 40 of FIG. 5A are shown. In the depicted embodiment, exterior portions of the lead receptacle are shown. In FIG. 5F, dashed lines represent conductive block 200 and bores 210, 220 formed therein. The receptacle includes alternating conductive 150 and insulating 160 sections. The conductive sections 150 are positioned such that when a lead is inserted into the receptacle, a contact on proximal portion may be electrically coupled with a conductive section 150. The conductive sections 150 of the receptacle are electrically coupled to feedthroughs 18 that couple the conductive sections 150 to electronics of the device. The block or block housing 47 of the receptacle is fixed relative to housing 45. The lead receptacle may also include an end cap 170. End cap 170 may fit snuggly against housing 45 or other feature such that an axially compressive force is applied to the receptacle.

Conductive block 200 is disposed within a cavity formed in the block or block housing 47 of the receptacle. The conductive block 200 defines a lead receiving bore 220 and a second bore 210. The second bore 210 is generally perpendicular to and intersects with the lead receiving bore 220. The lead receiving bore 220 may be axially aligned with bore 110 formed in the block or block housing 47 of the receptacle (see, e.g., FIG. 5B). Conductive block 200 is electrically coupled to a feedthrough 18 that serves to electrically couple the block 200 to electronics of the device.

Figure 5G:
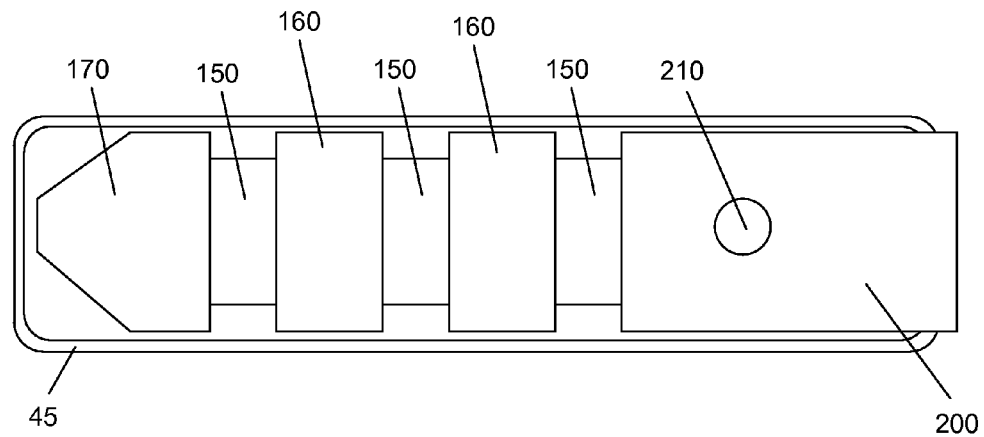
Figure 5H:
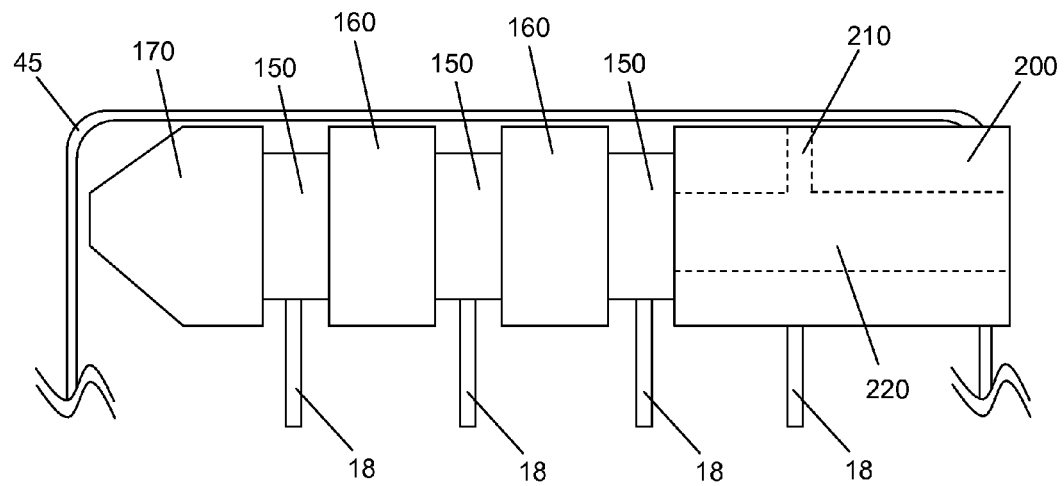

In FIGS. 5G-H, schematics of a cut away top view (5E) and a cut away side view (5F) of an alternative embodiment of the header 40 of FIG. 5A are shown. The embodiment depicted in FIGS. 5G-H are substantially similar to that shown in FIGS. 5E-F, except that block 200 is non-conductive and replaces the block 200 and block housing 47 shown in FIGS. 5E-F. In embodiments where block 200 is non-conductive, another component, such as a lead engagement member (see, e.g., FIGS. 7-9), is conductive and serves to electrically couple a lead to electronics of the device. Accordingly, a feedthrough 18 or conductive wire may be attached to the other component, such as the lead engagement member, to electrically couple the component to device electronics.

Figure 6A:
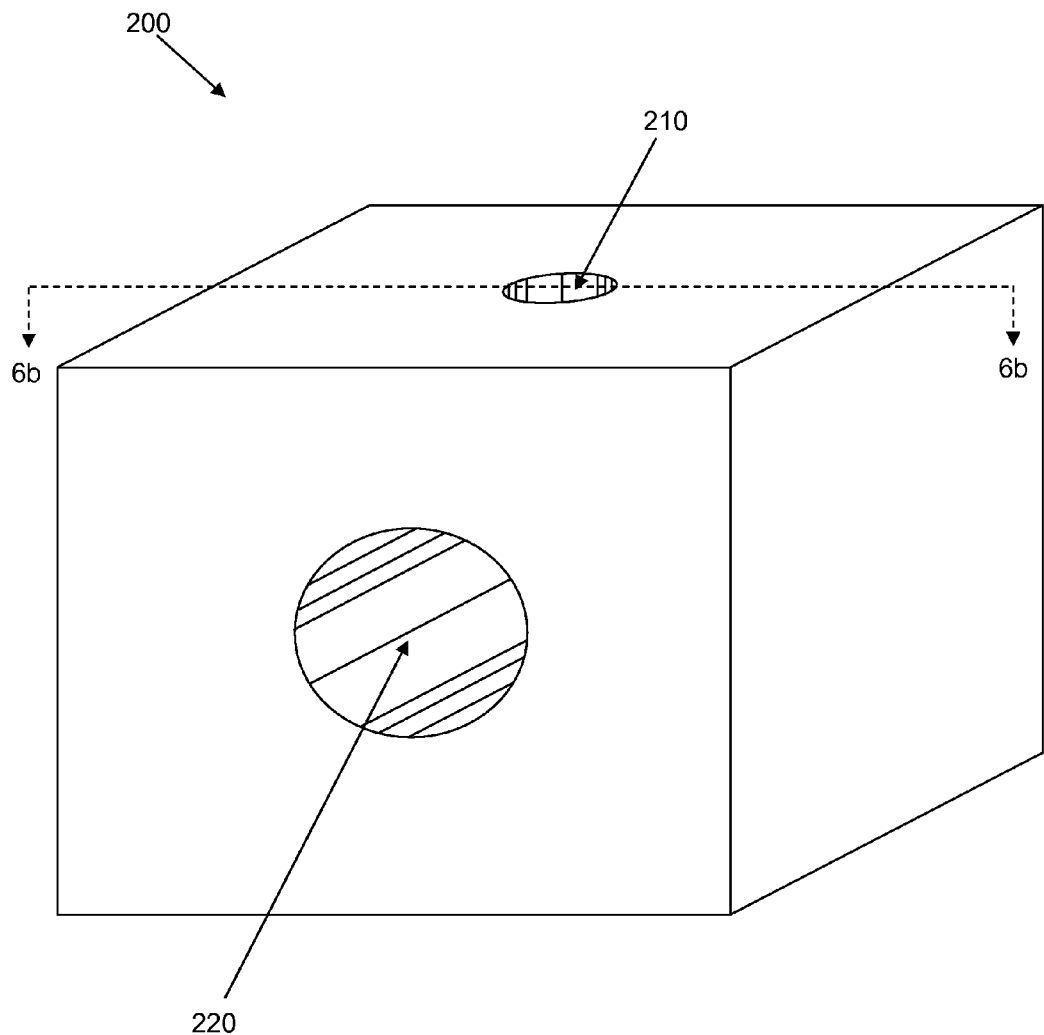
FIG. 6A is a schematic perspective view of a representative conductive block of a lead retention assembly.
Figure 6B:
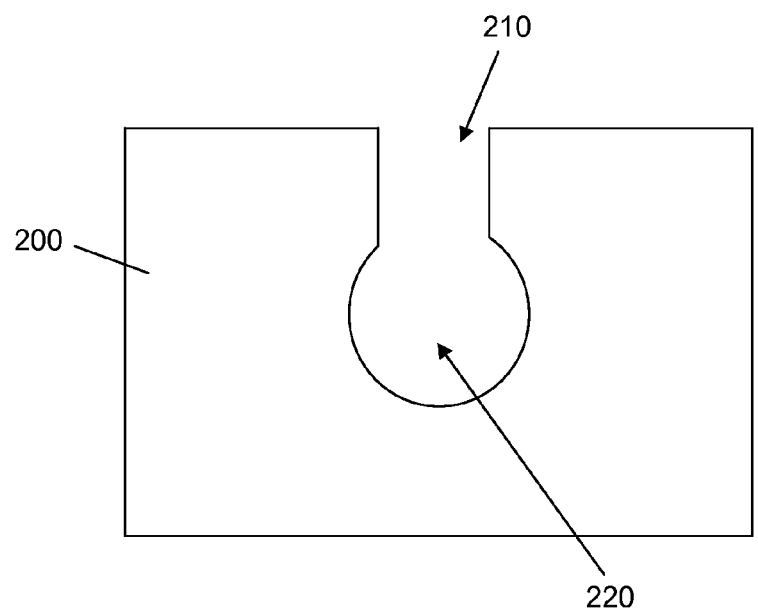
FIG. 6B is a schematic cross section of the block depicted in FIG. 6A taken along line 6b-6b.

In FIG. 6A, a schematic perspective view of a block 200, such as a block depicted in FIGS. 5E-H, is shown. In FIG. 6B, a cross section of the block 200 taken along line 6b-6b of FIG. 6A is shown. As with the block 200 depicted in FIGS. 5E-H, the block shown in FIGS. 6A-B defines a lead receiving bore 210 and a second bore 210 generally perpendicular to and intersecting with the lead receiving bore 220.

Figure 7A:
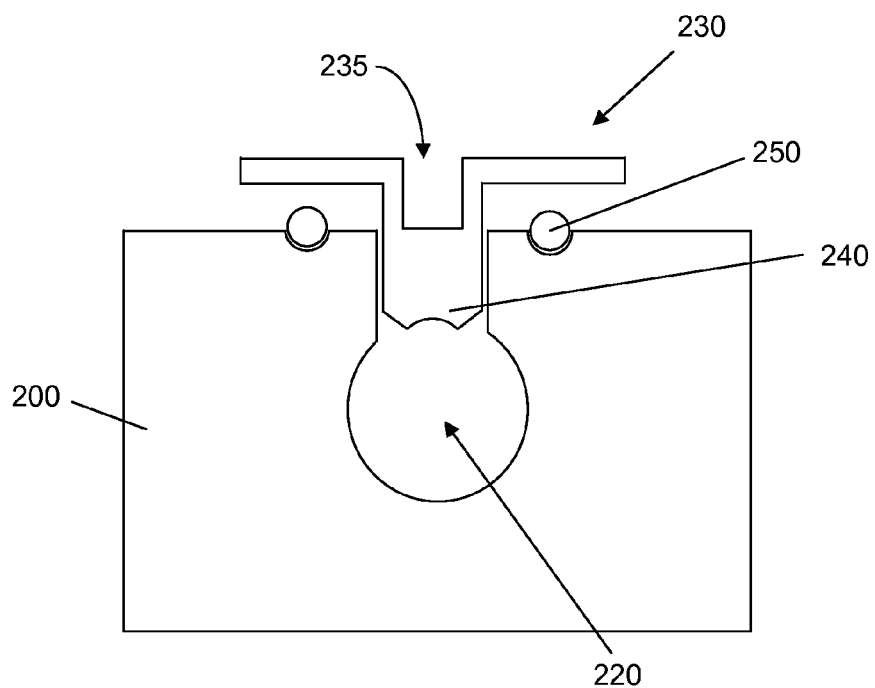
FIGS. 7-8 are schematic diagrams of cross sections of selected components of lead retention assemblies.

In FIG. 7A, a lead engagement member 230 having a lead engagement feature 240 is shown. The lead engagement feature is disposed within and moveable within the second bore 210. The lead engagement feature 240 may move in the bore 210 towards the lead receiving bore 220 such that, when a lead is received by the lead receiving bore 220, the lead engagement feature 240 engages the lead (or extension or adaptor), preferably at a contact 80 of the lead (see, e.g., FIGS. 2-3). In various embodiments, the lead engagement member 230 is formed from electrically conductive material. In embodiments where block 200 is conductive and electrically coupled to device electronics, a conductive lead engagement member 230 may facilitate an electrical connection between conductive block 200 and proximal contact 80 of lead. In some embodiments, a feedthrough or conductive wire electrically couples the lead engagement member 230 to device electronics. In some embodiments, the lead engagement member 230 is formed of non-conductive material. In other embodiments, the lead engagement member 230 is formed from both conductive and nonconductive materials where the lead engagement feature 240 is conductive and the surface of cavity 235 formed in engagement member 235 is nonconductive. Cavity 235 is configured to receive a set screw (not shown) in various embodiments. In embodiments where lead engagement member 230 or cavity 235 is nonconductive, lead engagement member 230 or cavity 235 may serve to electrically isolate the set screw from a conductive block 200. Regardless of whether the block 200 or lead engagement member 230 is conductive, as the set screw is advanced, the set screw causes the lead engagement feature 240 of lead engagement member 230 to move in the second bore towards the lead receiving bore 220.

As further shown in FIG. 7A, a sealing member 250, such as an O-ring, may be disposed within a recess or channel of block 200 to sealingly engage a portion of lead engagement member 230. As the lead engagement feature 240 of lead engagement member 230 moves in the second bore towards the lead receiving bore 220, a portion of lead engagement member may sealingly engage the sealing member 250. In various embodiments, the lead engagement member 230 is in contact with the sealing member 250 when set screw is not present or is not advanced.

Figure 7B:
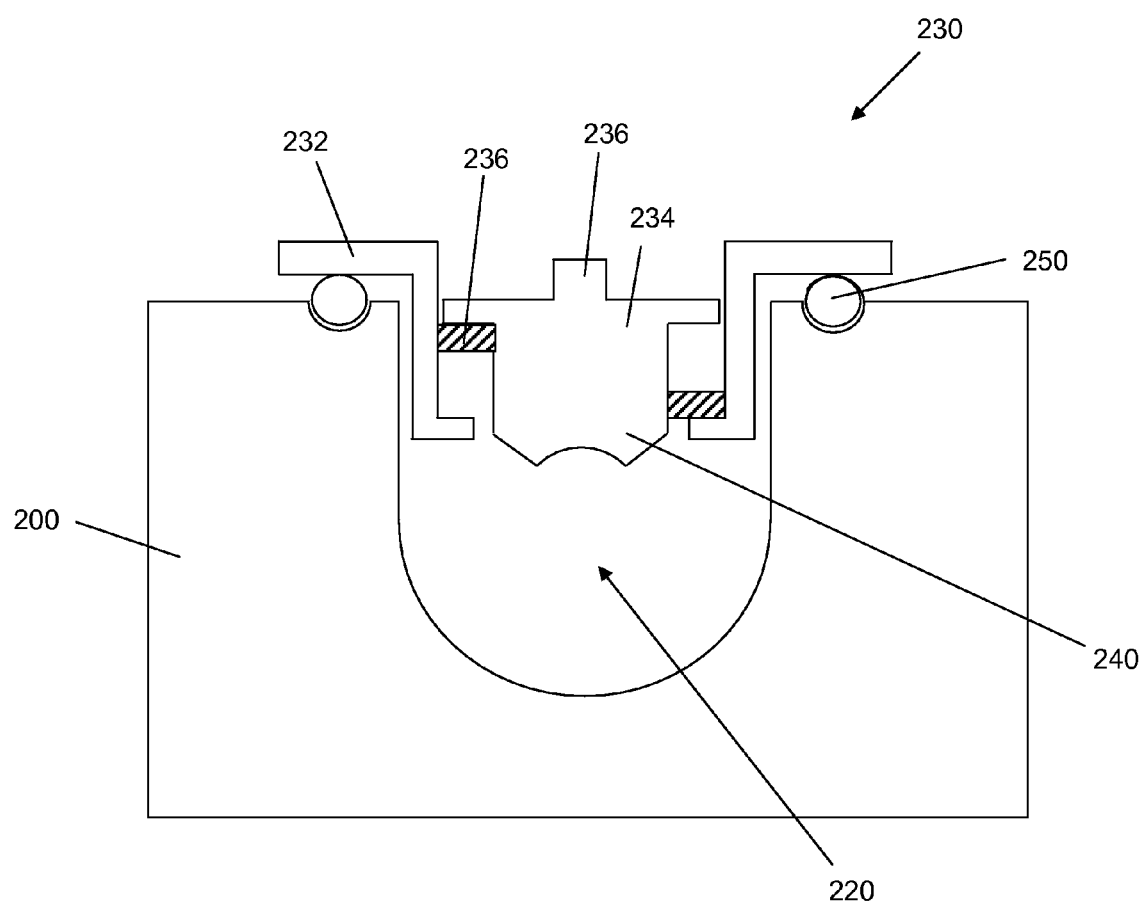

Referring now to FIG. 7B, an embodiment of a two-part lead engagement member 230 is shown. In the depicted embodiment, a first part 232 of the lead engagement member 230 is partially disposed within the second bore that is generally perpendicular to the lead receiving bore 220 of block 200 and includes a rim or flange to prevent the first part 232 from falling in the second bore. The second part 234 of the lead engagement member 230 is disposed within a cavity formed within the first part 232. The second part 234 includes the lead engagement feature 240 and is moveable within the cavity formed within the first part 232, and thus moveable within the second bore of the block 200, such that the lead engagement feature 240 is capable of engaging a lead within the bore 220 when a set screw (not shown) is tightened. The second part 234 may include a feature 236, depicted as a protrusion in the embodiment shown in FIG. 7B, that complementary to a non-conductive member (not shown—see, e.g., FIG. 8). A biasing member 236, such as a wave washer (depicted), spring, or the like, may be employed to bias the second part 234 away from lead receiving bore 220 to allow a lead to be inserted into bore 220. Once the lead is inserted in bore 220 the lead engagement feature 240 of second part 234 may be advanced in the second bore towards the lead receiving bore 220 to engage the lead, by advancing a set screw (not shown). Such multipart construction of lead engagement member 230 may be desirable where lead engagement member 230 is conductive and is electrically coupled device electronics. In such embodiments, first part 232 is preferably electrically coupled to the electronics.

Figure 8:
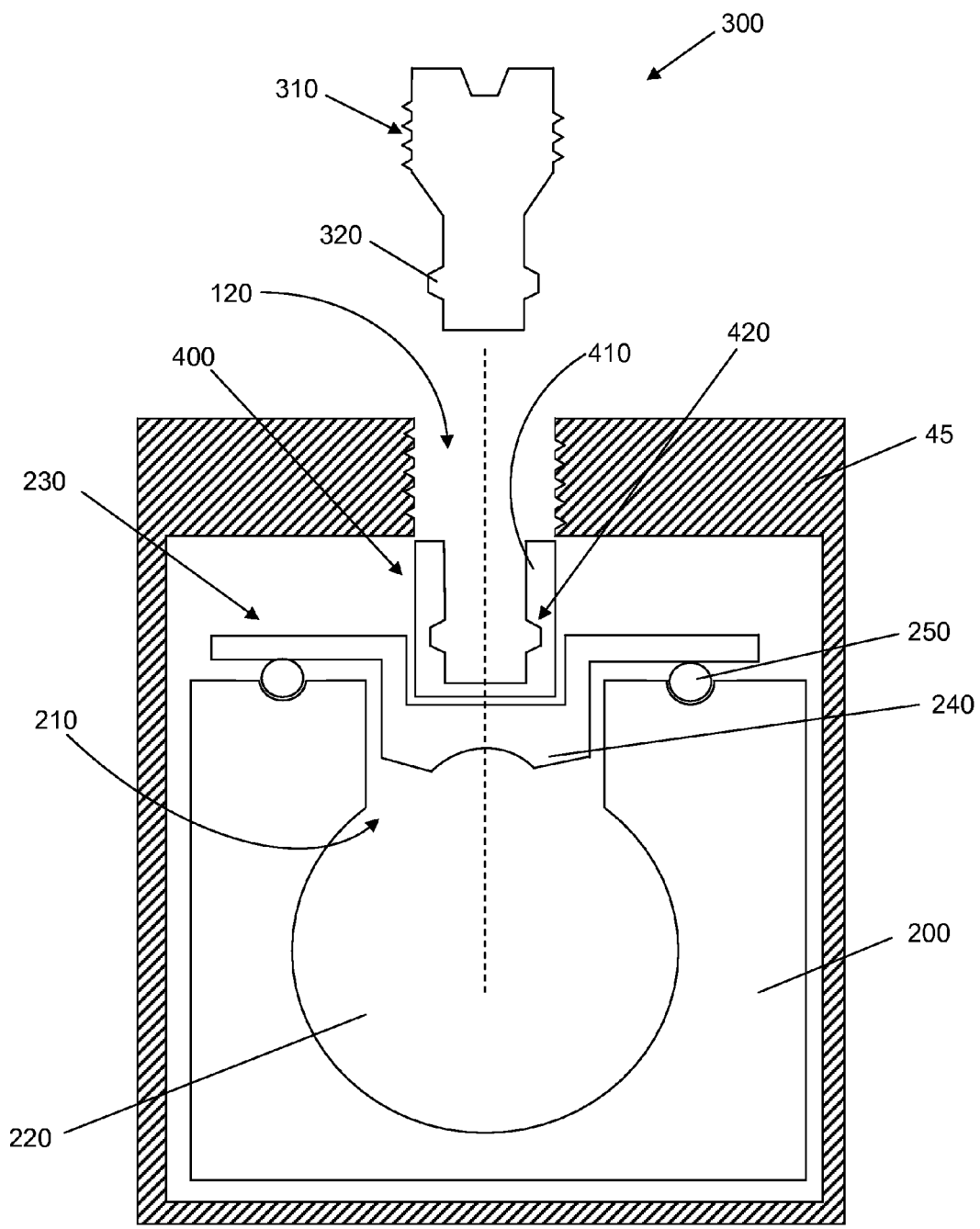

For the sake of convenience and simplicity, the lead engagement member 230 is discussed below and is shown in FIGS. 8-9 as a one piece member. However, it will be understood that the lead engagement member 230 may be a multipart member, e.g. as described with regard to FIG. 7B.

Referring now to FIG. 8, a schematic cross-section of a lead retention assembly is shown. The lead retention assembly in the depicted embodiment includes a conductive set screw 300, a housing 45, such as a header housing or a device housing, defining an opening 120, a lead engagement member 230, a nonconductive member 400, and a block 200 are shown. The set screw 300, the lead engagement member 230 and the nonconductive member 400 are shown in axial alignment. As with the embodiments depicted in FIGS. 5-7, the block 200 includes a lead receiving bore 220 and a second bore 210 generally perpendicular to and intersecting with the lead receiving bore 220. A lead engagement feature 240 of a lead engagement member 230 is disposed with and moveable within the second bore 210. The lead engagement member 230 forms a cavity configured to receive the nonconductive member 400. While not shown, it will be understood that the lead engagement member 230 may form a protrusion (see, e.g., FIG. 7B) or any other suitable feature and that the nonconductive member 400 may include any suitable complementary feature. In the depicted embodiment, the nonconductive member 400 includes sidewall 410 having an inner and outer surface. The inner surface of sidewall 410 forms a cavity configured to receive the set screw 300. In various embodiments, the nonconductive member 400 includes a set screw retention feature 420, such as a feature in the sidewall 410, configured to retain a complementary feature 320 of the set screw 300. The retention feature 420, in many embodiments, serves to prevent loosening migration of the set screw 300 relative to internally threaded opening 120 formed by housing 45. The set screw 300 includes an externally threaded portion 310 configured to threadingly engage the opening 120 defined by the housing 45. As the screw 300 is tightened relative to housing or advanced (movement toward the lead receiving bore 220), the set screw 300 causes the nonconductive member 400 to cause the lead engagement feature 240 of the lead engagement member 230 move within the second bore 210 toward the lead receiving bore 220. In the depicted embodiment, as screw 300 is tightened, lead engagement member 230 pushes down on O-ring 250, which is sufficiently compressible to allow sufficient advancement of lead engagement feature 240 towards lead receiving bore 220 to secure a lead within the bore 220.

In various embodiments, such as the embodiment shown in FIG. 8, the device and lead retention assembly are configured such that conductive set screw 300 is in fluid communication with tissue or fluid of a patient when implanted. For example, a portion of set screw 300 may protrude beyond the outer surface of housing 45. This is in contrast to typical set screw configurations where the set screw is electrically isolated from a patient's tissue or fluid by a nonconductive seal, such as a silicone grommet with a slit to allow for access of a screw driver to the screw, placed within an opening of a housing to prevent pocket stimulation. Pocket stimulation is unintended stimulation of tissue within the tissue pocket in which an active electrical device is implanted, as opposed to intended stimulation via an electrode disposed on a lead. Pocket stimulation occurs when an electrical signal generated by an active electrical device is delivered via an active set screw block, i.e. a set screw block that electrically couples a lead to the electronics of the active device, through a set screw to the patient's tissue. The embodiment depicted in FIG. 8 and other embodiments described and contemplated herein where set screw is in fluid communication with, and thus electrically coupled to, a patient's tissue would typically be considered undesirable. However, because the screw 300 is electrically isolated or insulated from the conductive block 200 or a conductive lead engagement member 230, which is electrically coupled to the device electronics, pocket stimulation may be eliminated or reduced by embodiments discussed or contemplated herein.

Figure 9A:
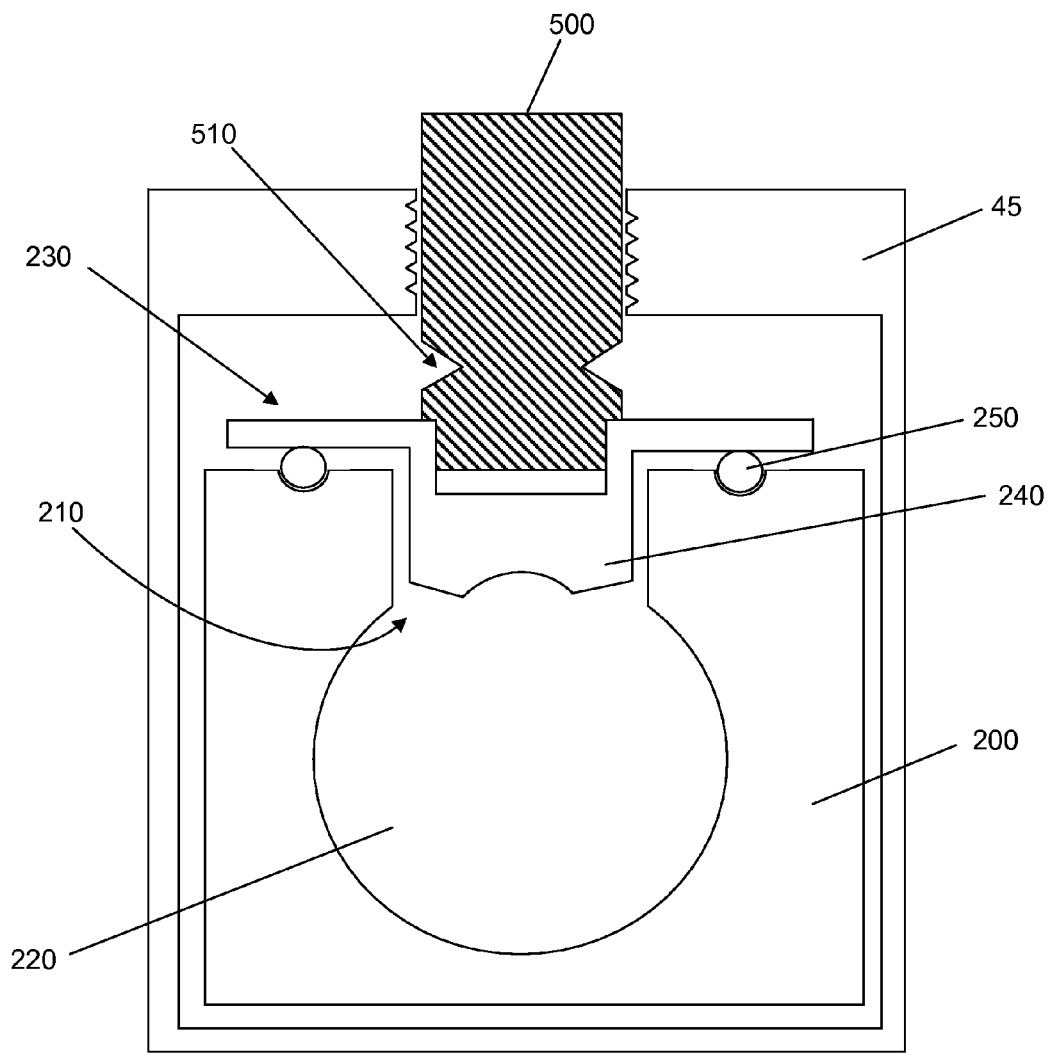
FIG. 9A is a schematic diagram of a cross section of selected components of a lead retention assembly and a molding pin.
Figure 9B:
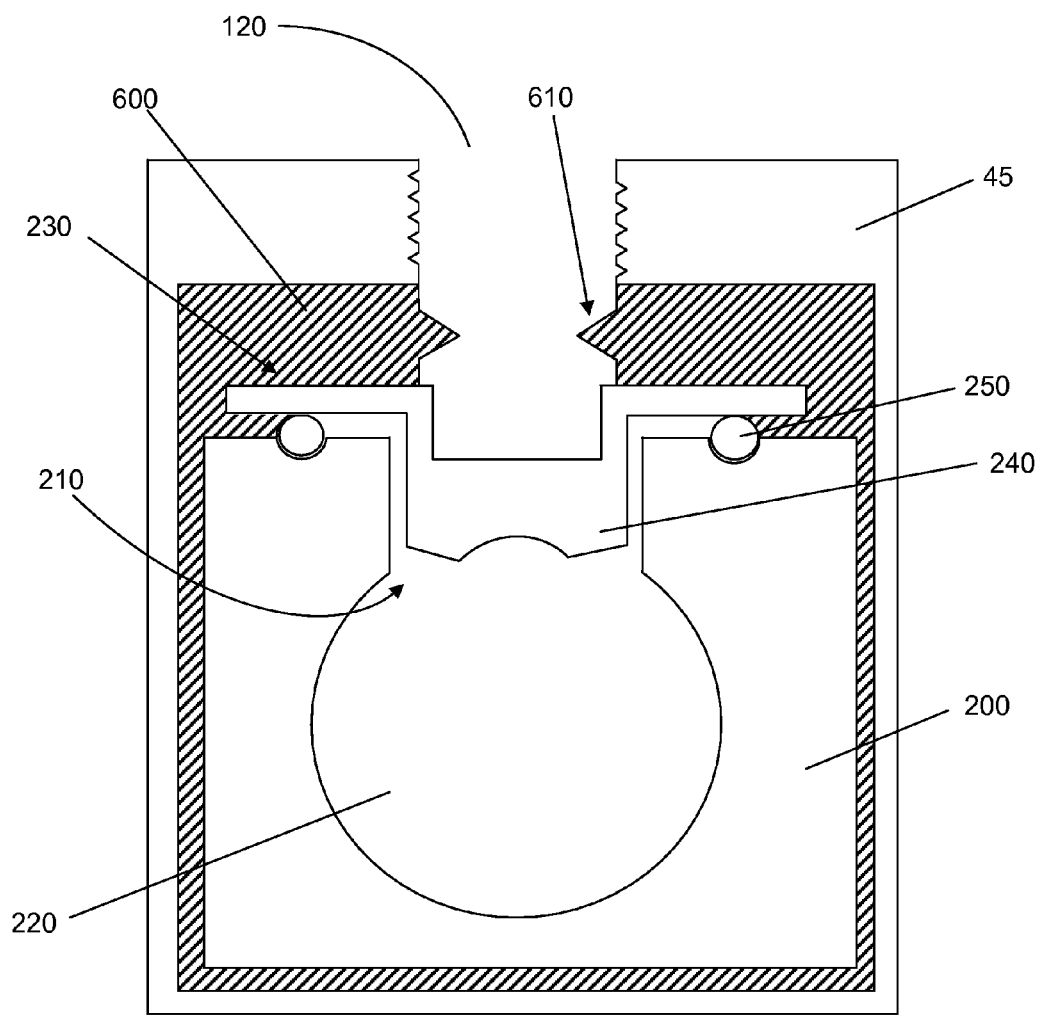
FIG. 9B is a schematic diagram of a cross section of the lead retention assembly of FIG. 9A with the molding pin removed and showing sealing material.
Figure 9C:
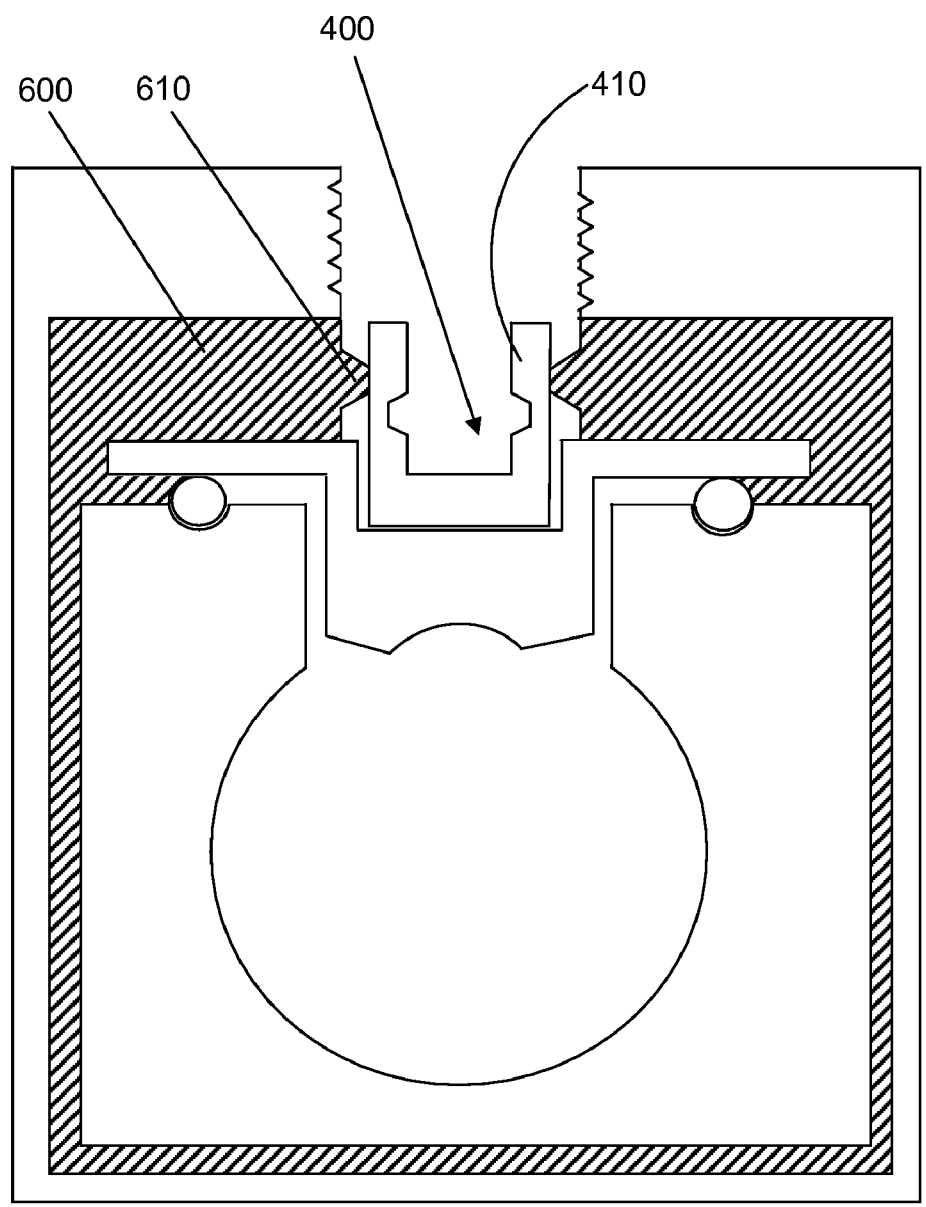
FIG. 9C is schematic diagram of a cross section of the lead retention assembly of FIG. 9B also showing a nonconductive member.

Referring now to FIG. 9A, a schematic cross section of selected parts of a lead retention assembly are shown. A housing 45, a block 200 and a lead engagement member 230 are depicted. The block 200 includes a lead receiving bore 220 and a second bore 210 generally perpendicular to and intersecting with the lead receiving bore 220. A lead engagement feature 240 of a lead engagement member 230 is disposed within the second bore 210. A sealing member 250 is disposed between and seals a portion of the lead engagement member 230 and the block 200. A molding pin 500 is disposed through an internally threaded opening of housing 45 and engaged with lead engagement member 230. Molding pin 500, which may be formed of any suitable material such as stainless steel, polyether ether ketone or polysulfone, has seal molding features 510 that are disposed between housing and lead engagement member 230. In the configuration shown, medical adhesive, silicone, or other polymeric material may be flowed through the housing to seal the components. For example, if housing is enclosed, the sealing material may be introduced through a hole 49 as depicted in the schematic back view of FIG. 5C. Seal molding features 510 of molding pin 500 mold polymeric wiper seals 610 of sealing material 600 (see FIG. 9B). As shown in FIG. 9C, wiper seals 610 of sealing member 600 engage exterior surface of sidewall 410 of nonconductive member 400.

It will be understood that the lead retention assemblies described herein are applicable to devices having headers that are not fully enclosed by a housing. Such headers are well known and are typically open-faced. Lead receptacles are typically sealed to such header housings with medical adhesive and are back-filled with medical polymeric material, such as silicone, to provide a seal between the electrically conductive portions of the lead receptacle and tissue or fluid of a patient when implanted.

Regardless of whether headers are open-faced or enclosed, the headers as described herein in various embodiments may be formed from conductive, nonconductive or composite material. Examples of conductive material that may be used to form a header include platinum, platinum iridium, titanium, tantalum, nickel-cobalt-molybdenum alloys, or the like. Examples of nonconductive materials that may be used to form a header housing include polyurethane, polysulfone, polycarbonate, polyether ether ketone, or the like. Lead engagement members and blocks may also be made of similar conductive or nonconductive materials.

A nonconductive member, as described herein, may be made of any suitable nonconductive material. For example, nonconductive member may be formed from a nonconductive polymer, such as silicone, polyurethane, polysulfone, polycarbonate, polyether ether ketone, or the like.

Components as described herein may be formed by any suitable process. For example, various components may be molded, machined, or otherwise formed.

While a space is shown between various components throughout the drawings, e.g. between bore 210 and lead engagement member 230 or lead engagement member 230 and O-ring 250, it will be understood that the various components may be in contact or may be spaced apart as shown.

Thus, embodiments of the HEADER FOR IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A lead retention assembly for an implantable medical device, comprising:
    a conductive set screw;
    a housing defining an opening for receiving at least a portion of the set screw;
    a block disposed within the housing and defining a lead receiving bore and a second bore extending generally perpendicular to and intersecting with the lead receiving bore; and
    a conductive lead engagement member having a lead engagement feature, wherein the lead engagement feature is disposed within and movable within the second bore such that advancement of the set screw causes the lead engagement feature to move within the second bore towards the lead receiving bore,
    wherein the set screw is electrically isolated from the conductive lead engagement member.

2. The assembly of claim 1, further comprising a nonconductive member configured to at least in part electrically isolate the set screw from the conductive lead engagement member, wherein the nonconductive member is disposed within the housing such that advancement of the set screw causes the nonconductive member to cause the lead engagement feature to move within the second bore towards the lead receiving bore.

3. The assembly of claim 2, wherein the nonconductive member comprises a set screw retention feature.

4. The assembly of claim 2, wherein the lead engagement member, the nonconductive member and the set screw are disposed in axial alignment.

5. The assembly of claim 2, further comprising a sealing member disposed within the housing,
   wherein the nonconductive member has (i) an exterior surface and (ii) interior surface defining a cavity configured to receive at least a portion of the set screw, and
   wherein the sealing member sealingly engages the exterior surface of the nonconductive member.

6. The assembly of claim 1, wherein the opening defined by the housing is internally threaded and configured to engage a threaded portion of the set screw.

7. The assembly of claim 6, wherein the housing is formed from conductive material.

8. The assembly of claim 1, wherein the assembly is configured such that the set screw is exposed to bodily fluid when the header is implanted in a patient.

9. An implantable medical device comprising:
   an assembly according to claim 1;
   a hermetically sealed device housing attached to the housing of the assembly;
   electronics disposed within the device housing,
   wherein the electronics are electrically coupled to the conductive lead engagement member.

10. The device of claim 9, wherein the assembly housing and the device housing together form a hermetically sealed internal chamber.

11. A method for manufacturing a lead retention assembly for an implantable medical device, the method comprising:
    axially aligning a second bore of a block with an opening in a housing of the assembly, the block defining the second bore and a lead receiving first bore, the second bore extending generally perpendicular to and intersecting with the lead receiving bore, wherein the opening of the housing is configured to threadingly engage a set screw;
    placing a lead engagement feature of a conductive lead engagement member within the second bore of the conductive block;
    inserting a molding pin through the opening pin and pressing the engagement feature towards the conductive block;
    flowing a sealing material into the housing and around the molding pin;
    removing the molding pin to create a cavity formed by the sealing material, wherein the cavity is in communication with the opening and is axially aligned with the opening and the lead engagement member; and
    placing a nonconductive member in the cavity between the opening of the housing and the lead engagement member, wherein the nonconductive member comprises an exterior surface and interior surface defining a set screw receiving cavity, wherein the nonconductive member is placed in the cavity formed by the sealing material such that exterior surface of the nonconductive member sealingly engages the sealing material.

12. The method of claim 11, further comprising threading the set screw through the opening of the housing such that a portion of the set screw is received in the cavity formed by the interior surface of the nonconductive member.

13. A method for manufacturing a medical device, comprising:
    manufacturing the assembly according to the method of claim 11; and
    operably coupling the conductive lead engagement member of the assembly to electronics of the device.

14. A lead retention assembly for an implantable medical device, comprising:
    a conductive set screw;
    a housing defining an opening for receiving at least a portion of the set screw;
    a conductive block disposed within the housing and defining a lead receiving bore and a second bore extending generally perpendicular to and intersecting with the lead receiving bore; and
    a lead engagement member having a lead engagement feature, wherein the lead engagement feature is disposed within and movable within the second bore such that advancement of the set screw causes the lead engagement feature to move within the second bore towards the lead receiving bore,
    wherein the set screw is electrically isolated from the conductive block.

15. The assembly of claim 14, wherein the lead engagement member is non-conductive, wherein the lead engagement member at least in part electrically isolates the set screw from the conductive block.

16. The assembly of claim 14, further comprising a nonconductive member configured to at least in part electrically isolate the set screw from the conductive block, wherein the nonconductive member is disposed within the housing such that advancement of the set screw causes the nonconductive member to cause the lead engagement feature to move within the second bore towards the lead receiving bore.

17. The assembly of claim 16, further comprising a sealing member disposed within the housing,
    wherein the nonconductive member has (i) an exterior surface and (ii) interior surface defining a cavity configured to receive at least a portion of the set screw, and
    wherein the sealing member sealingly engages the exterior surface of the nonconductive member.

18. The assembly of claim 14, wherein the opening defined by the housing is internally threaded and configured to engage a threaded portion of the set screw.

19. The assembly of claim 18, wherein the housing is formed from conductive material.

20. The assembly of claim 14, wherein the assembly is configured such that the set screw is exposed to bodily fluid when the header is implanted in a patient.

* * * * *